United States Patent [19]
Darsow

[11] Patent Number: 6,020,472
[45] Date of Patent: *Feb. 1, 2000

[54] PROCESS FOR PREPARING α-D-GLUCOPYRANOSIDO-1,6-MANNITOL AND-SORBITOL FROM α-D-GLUCOPYRANOSIDO-1,6-FRUETOSE

[75] Inventor: Gerhard Darsow, Krefeld, Germany

[73] Assignee: Bayer Aktiengesellschaft, Leverkusen, Germany

[*] Notice: This patent is subject to a terminal disclaimer.

[21] Appl. No.: 08/926,118

[22] Filed: Sep. 9, 1997

[30] Foreign Application Priority Data

Sep. 10, 1996 [DE] Germany .................. 196 36 625

[51] Int. Cl.$^7$ .............. C07H 1/00; C07H 15/00; C07C 27/00; B01J 31/00
[52] U.S. Cl. ............ 536/18.5; 536/1.11; 536/4.1; 536/124; 568/863; 502/102; 585/250
[58] Field of Search .................. 536/18.5, 1.11, 536/4.1, 124; 568/863; 502/102; 585/250

[56] References Cited

U.S. PATENT DOCUMENTS

| | | |
|---|---|---|
| 3,865,957 | 2/1975 | Schieweck et al. .......... 426/213 |
| 4,117,173 | 9/1978 | Schiweck et al. .......... 426/548 |
| 4,684,720 | 8/1987 | Darsow et al. .......... 536/124 |
| 5,644,044 | 7/1997 | Darsow .................. 536/185 |
| 5,679,781 | 10/1997 | Goldscher .............. 536/18.5 |

FOREIGN PATENT DOCUMENTS

| | | | |
|---|---|---|---|
| 0152779A2 | 8/1985 | European Pat. Off. ........ C07H 15/04 |
| 2217628 | 10/1973 | Germany .......... C07C 31/26 |
| 02520173 | 12/1976 | Germany .......... C07H 3/04 |
| 4416115 | 11/1995 | Germany .......... C07C 31/26 |

*Primary Examiner*—Gary L. Kunz
*Assistant Examiner*—Everett White
*Attorney, Agent, or Firm*—Sprung Kramer Schaefer & Briscoe

[57] ABSTRACT

The sugar alcohols mentioned as title compounds can be prepared from the corresponding sugar in equimolar amounts by catalytic hydrogenation with hydrogen in aqueous solution, the hydrogenation being carried out continuously at an $H_2$ pressure of 100 to 400 bar and a reaction temperature of 20 to 80° C. using fixed-bed support-free molded bodies composed of compacted powders of alloys of the elements of the iron subgroup of group VIIIA of the periodic table with elements of group IVB and VA. The molded bodies have a compressive strength of 20 to 220 N and an internal surface area of 10 to 95 $m^2/g$.

18 Claims, No Drawings

PROCESS FOR PREPARING α-D-GLUCOPYRANOSIDO-1,6-MANNITOL AND-SORBITOL FROM α-D-GLUCOPYRANOSIDO-1,6-FRUETOSE

BACKGROUND OF THE INVENTION

1. Field of the Invention

The invention relates to an inexpensive process for preparing an equimolar mixture of the diastereomeric sugar alcohols α-D-glucopyranosido-1,6-mannitol and α-D-glucopyranosido-1,6-sorbitol from α-D-glucopyranosido-1,6-fructose by continuous catalytic hydrogenation with hydrogen.

The course of the reaction can be illustrated by the following reaction diagram:

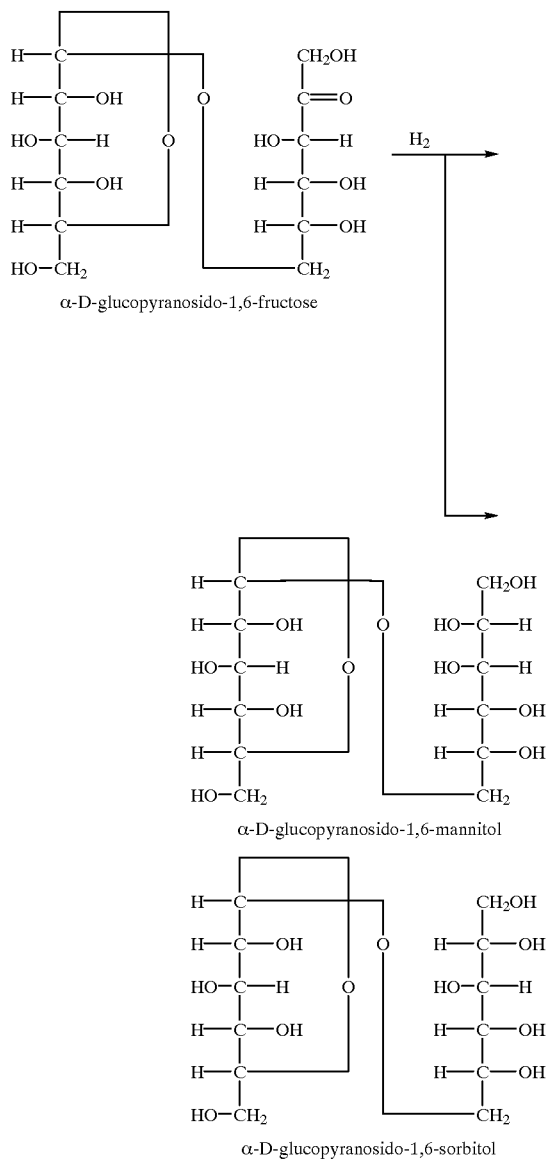

α-D-glucopyranosido-1,6-fructose

α-D-glucopyranosido-1,6-mannitol

α-D-glucopyranosido-1,6-sorbitol

2. Description of the Related Art

In the known processes for preparing α-D-glucopyranosido-1,6-sorbitol (German Patent Specification 2 217 628) and α-D-glucopyranosido-1,6-mannitol (German Auslegesschrift 2 520 173), a powdered nickel catalyst is used in each case in the discontinuous suspension process (batch process) as hydrogenation catalyst. Discontinuous processes have the disadvantage that their capacity is very small relative to the reaction volume and, consequently, there is a need for large-volume, expensive reaction equipment and storage tanks. Energy consumption and staff requirements are comparatively high in discontinuous processes. Continuous powdered catalyst processes which employ a plurality of hydrogenation reactors connected in cascade avoid some of these disadvantages. It remains necessary, however, to add the powdered catalyst in a controlled manner, to circulate it by pumping and to filter it off quantitatively from the reaction product. The catalyst sludge pumps are subject to a high mechanical wear. The quantitative removal of the powdered catalyst from the reaction product is expensive. Furthermore the danger of reducing the catalyst activity as a result of the additional operations very rapidly is great. It is therefore advantageous to arrange for the reaction to proceed over a fixed catalyst. Such a catalyst must have a high activity which must not diminish over a prolonged period of time because frequent catalyst replacements in fixed-bed reactions are also expensive.

EP-A 152 779 discloses a process for the continuous hydrogenation of α-D-glucopyranosido-1,6-fructose to form a mixture of the sugar alcohols α-D-glucopyranosido-1,6-mannitol and -sorbitol over support-free molded bodies of elements of group VIIIA of the periodic table, in which said support-free molded bodies are preferably produced by compacting and/or bonding metal powders.

DE-A 4 416 115 discloses a process for the continuous hydrogenation of α-D-glucopyranosido-1,6-fructose to form a mixture of the corresponding sugar alcohols over support-free molded bodies of the iron subgroup of group VIIIA of the periodic table with elements of group VIA. Unfortunately, in these processes, the two sugar alcohols are not produced in equimolar amounts, which would be desirable for physical reasons (always the same freezing point of the mixture) and is necessary for use in pharmaceutical applications (prescribed establishment of the composition), but in different quantitative ratios in each case depending on reaction temperature. It is furthermore desirable to increase the hourly catalyst loading markedly and to reduce the catalyst costs further. In addition, it is always desirable to carry out a process at the lowest possible temperature in order to reduce energy costs.

SUMMARY OF THE INVENTION

Surprisingly, it has now been found that, after their compaction to form molded bodies, nickel, cobalt and iron alloy metal powders containing elements of group IVB and VA of the periodic table and originating from cheap alloying wastes not only successfully catalyze the hydrogenation of α-D-glucopyranosido-1,6-fructose to an equimolar mixture of α-D-glucopyranosido-1,6-mannitol and α-D-glucopyranosido-1,6-sorbitol, but that catalysts composed of these metal alloys, which are 50–70% less expensive than pure metals, also have an appreciably higher hydrogenation activity so that the hydrogenation reaction can be carried out at a reaction temperature up to 50° C. lower than previous processes. At the same time, the powders used may even contain in addition certain contaminations with other non-catalytically active elements or element alloys (for example manganese, silicon, aluminum) without the high activity being reduced.

The invention therefore relates to a process for preparing an equimolar mixture of α-D-glucopyranosido-1,6-mannitol and α-D-glucopyranosido-1,6-sorbitol from α-D-glucopyranosido-1,6-fructose by catalytic hydrogenation in aqueous solution with hydrogen under elevated pressure and at elevated temperature, which comprises carrying out the hydrogenation continuously at a hydrogen pressure of 100 to 400 bar and a temperature of 20 to 80° C. using the fixed-bed process over support-free molded bodies which act as hydrogenation catalysts, have a compressive strength of 20 to 220 N and an internal surface area of 10 to 95 m²/g and are composed of (i) one or more elements of the iron subgroup of group VIIIA of the periodic table of elements (Mendeleyev), which element or elements is/are additionally alloyed with (ii) elements of group IVB and/or VA of the periodic table of elements (Mendeleyev) which have activating action.

DETAILED DESCRIPTION OF THE INVENTION

The iron subgroup of group VIIIA of the periodic table of elements (Mendeleyev) contains the elements iron, cobalt and nickel. The support-free molded bodies to be used according to the invention contain one or more of these metals individually or in alloyed form, preferably in alloyed form in amounts of at least 50, preferably at least 60, in particular at least 70% by weight, relative to the total weight of the support-free molded bodies.

Group IVB of the periodic table contains the elements titanium, zirconium and hafnium. Group VA of the periodic table contains the elements vanadium, niobium, tantalum. The support-free molded bodies to be used according to the invention contain one or more of these elements individually or in alloyed form, preferably in alloyed form, with the elements of group VIIIA in amounts of at least 1.5, preferably at least 3.0, in particular at least 6.0% by weight, relative to the total weight of the support-free molded bodies; they contain one or more of said elements in amounts of not more than 30, preferably not more than 20 and, in particular, not more than 15% by weight, relative to the total weight of the support-free molded bodies.

In addition, the support-free molded bodies to be used according to the invention may contain, in each case relative to the total weight of the support-free molded bodies, up to 20, preferably up to 18, in particular up to 15% by weight of other elements individually or in alloyed form; examples of such elements, which must not be catalytically active, comprise aluminum, silicon and manganese. According to a preferred embodiment, the support-free molded bodies contain, in addition to the components (i) and (ii), not more than 12% by weight of aluminum and not more than 5% by weight of other elements apart from Al.

The support-free molded bodies can be produced by conventional methods by compacting powdered elements having particle sizes of up to 200 μm on tabletting or pelleting machines under high pressure, in which process, to improve the adhesion of the metal particles, graphite in amounts of 0.5–1.5% by weight, relative to the total weight of the constituents forming the catalyst, or adhesives in similar amounts may also be used. For the purpose of production, powders of the elements provided may be mixed and compacted; it is, however, also possible to use powders composed of suitable alloys. Such alloys either have the appropriate composition or one in the vicinity which is adjusted by supplementary additions of suitable elements. For this purpose, alloying wastes and residues of any origin can be used. The support-free molded bodies are preferably produced in an oxygen-free atmosphere in order to avoid surface oxidation. Tabletted or pelleted molded bodies having dimensions of 3 to 7 mm are the most effective and the most beneficial for conducting the reaction. Of appreciable importance is the compressive strength of the molded bodies, which, according to the invention, has values of 20 to 220 N, preferably 110 to 220 N. Lower compressive strengths could result in molded-body disintegration or erosive abrasion, which would bring about a metallic contamination of the reaction product. Of appreciable importance, furthermore, is the internal surface area of the molded bodies which, according to the invention, has values of 10 to 95 m²/g and is crucial for as quantitative a conversion as possible of the feedstocks. The compacted molded bodies have macroscopically smooth exterior surfaces.

The compressive strength of the support-free molded bodies can be determined in accordance with DIN 50 106 and is understood as meaning compressive strength on the arched molded surfaces. The testing of support-free molded bodies for the claimed internal surface area and, consequently, for usability for the process according to the invention can be carried out by methods which have been described by F. M. Nelsen and F. T. Eggertsen, Analyt. Chem. 30 (1958), 1387 or S. J. Gregg and S. W. Sing, Adsorption, Surface Area and Porosity, London 1967, Chapters 2 and 8.

It is possible, by the process according to the invention, to prepare the crystallized mixture of the two diasteriomeric sugar alcohols without further purification operations in a purity of over 99.5% by weight, the content of unconverted α-D-glucopyranosido-1,6-fructose being ≦0.1% by weight and the sum of sorbitol and mannitol being less than 0.3% by weight. The two sugar alcohols are produced in an essentially equimolar mixture; this means a mixture in the range from 49 to 51:51 to 49% by weight.

Crystalline α-D-glucopyranosido-1,6-fructose is used as starting compound for the process according to the invention. This substance can be prepared from saccharose solution by enzymatic conversion using living or immobilized cell systems by known methods (for example, German Patent Specification 1 049 800). The α-D-glucopyranosido-1,6-fructose is advantageously dissolved in oxygen-free, deionized water. The procedure is, for example, as follows: from α-D-glucopyranosido-1,6-fructose and deionized drinking water, a 15 to 60% by weight, preferably 40 to 55% by weight, aqueous solution is prepared whose pH is adjusted to 4.5–11.5, preferably 5–8.5. When dissolved in water having a pH of 7, crystalline α-D-glucopyranosido-1,6-fructose exhibits either a neutral or, as a result of trace gluconic acid formation possibly caused by Cannizarro reaction, a weakly acidic reaction. The desired pH adjustment can be carried out, for example, by adding as pure as possible organic acids, such as citric acid, sorbic acid, and also sugar acids or by adding $(NH_4)_2CO_3$ salt to the aqueous solution.

Pure hydrogen precompressed to a pressure of 100 to 400 bar, preferably 200 to 300 bar is used in a 1–20 times molar, preferably 1–10 times molar amount for the hydrogenation process. The hydrogenation is carried out continuously using the fixed-bed process on the support-free molded bodies of a metallic nature used as hydrogenation catalysts by either allowing the solution to be hydrogenated with the previously admixed hydrogen to flow from the bottom or top over the molded bodies loaded into a hydrogenation reactor (co-current process) or, alternatively, to flow from the bottom in opposition to the hydrogen flowing in from the top or vice versa (countercurrent process). The hydrogenation reactor may either be a single high-pressure steel or steel-alloy tube completely or partly filled with support-free molded bodies, in which case arrangement on trays, wire baskets or the like may also be useful or, alternatively, a jacketed high-pressure tube bundle whose individual tubes are filled with molded bodies in the manner mentioned.

The hydrogenation process is carried out at a temperature of 20 to 80° C., preferably 40 to 70° C. Lower temperatures necessitate either higher dwell times or dispensing with a quantitative conversion of the α-D-glucopyranosido-1,6-fructose. Higher temperatures result in increased formation of sugar monoalcohols (sorbitol or mannitol) and also in uncontrolled side reactions (caramelization, hydrocracking), which may result in discoloration and also in the formation of further undesirable byproducts. The hourly catalyst loading may be 45 to 550 g of α-D-glucopyranosido-1,6-fructose/l of catalyst. In the reaction conditions described, quite unexpectedly high catalyst service lives of 15,000 hours and over can be achieved, which results in catalyst consumption of ≦0.12% by weight, relative to the reaction product.

Consequently, in addition to the high yields of α-D-glucopyranosido-1,6-mannitol and α-D-glucopyranosido-1,6-sorbitol in equimolar amounts and of a purity of the mixture which renders further purification procedures unnecessary, the principal technical advantages of the process recording to the invention lie particularly in the low catalyst costs and the low reaction temperature.

After letting down, during which process the excess hydrogen is collected which, after recompression, can be used again, the hydrogenated aqueous solution leaving the reactor which contains the two sugar alcohols α-D-glucopyranosido-1,6-mannitol and -sorbitol in a ratio of 1:1, is filtered and can already be used in this form directly as sugar exchange mixture for dietetic purposes in liquid form. The water in the solution can, however, also be removed in a known manner by means of spray driers, drying rollers or freeze drying. As a rule, the colorless and glass-clear solution obtained after the filtration is concentrated in a falling-film evaporator or an apparatus which functions similarly to a sugar alcohol content of approximately 80% by weight and then crystallized completely in a vacuum crystallization apparatus. The crystallized material can be reduced to a uniform particle size by a subsequent grinding process and optional sieving. Although the product thus obtained is flowable and appears completely dry, it has a content of water of crystallization of approximately 5% by weight, which is attributable to the fact that α-D-glucopyranosido-1,6-mannitol, in contrast to α-D-glucopyranosido-1,6-sorbitol, crystallizes with a content of about 10% by weight of water of crystallization. The product obtained starts to melt at 95° C. A clear melt is formed at 141° C. The precise melting range of the anhydrous mixture of substances is obtained if, for example, the water-containing product is melted in an evacuable drying apparatus at 110° C. and 10 mbar and the water is allowed to evaporate quantitatively from the melt. A recrystallized sample treated in this way has a melting range of 140 to 143° C.

The two sugar alcohols which can be prepared equimolarly according to the invention are known in regard to their field of application. They are used as individual substances and as a mixture because of their pleasantly sweet taste, which is free from after taste or side taste, in contrast to some other sugar alcohols, as low-calorie sugar substitutes which are also suitable for diabetics and less cariogenic than saccharose.

In its solution behaviour in water, the equimolar mixture of α-D-glucopyranosido-1,6-mannitol and α-D-glucopyranosido-1,6-sorbitol is between that of the pure substances in the temperature range from 0 to 70° C. At temperatures above 70° C., the solubility of the mixture exceeds that of the pure substances, which makes the use of the mixture as sweetening agent for drinks and foodstuffs always appear particularly advantageous if the substances in question have to be sweetened more strongly. Not only the individual compounds, which are obtainable, for example, by fractional crystallization, but also the mixture exhibits a sweetening strength which corresponds to approximately 45% of the sweetening strength of saccharose. To increase the sweetening strength of the equimolar mixture of α-D-glucopyranosido-1,6-mannitol and α-D-glucopyranosido-1,6-sorbitol, artificial sweeteners, for example cyclohexyl sulfamate or phenylalanine/methyl asparagate, can be added to the aqueous solution and obtained in crystalline form by combined vacuum crystallization. Artificial sweeteners in solid form can, however, also be mixed with the crystallized material. The mixture of α-D-glucopyranosido-1,6-mannitol and α-D-glucopyranosido-1,6-sorbitol can also be mixed in liquid or solid form with other sweet-tasting sugar alcohols, for example sorbitol, xylitol, mannitol and/or lactitol. Owing to its high caramelization point, the mixture is particularly well suited as a sweet-tasting, structure-forming and body-forming filler for chocolate, marzipan, chocolate candies and cookies.

EXAMPLES (The Percentages Relate to the Weight)

Example 1

A vertical-standing, thermally insulated stainless-steel high-pressure tube having an internal diameter of 45 mm and a length of 1 m was filled with 1.41 of a hydrogenation catalyst which was produced by tabletting powder of a Ni/Zr alloy having a Zr content of 19.8% and which, given a cylinder height of 5 mm and a diameter of 5 mm, had a compressive strength of 109 N and an internal surface area of 74 $m^2/g$. Together with the three times molar amount of high-purity hydrogen under a pressure of 300 bar, 300 ml of a 40%-strength solution of α-D-glucopyranosido-1,6-fructose in deionized drinking water which had been adjusted to a pH of 6.0, were continuously pumped per hour, ascending from the bottom upwards, through said tube. Aqueous solution and hydrogen were passed through a heat exchanger and heated to such an extent that they entered the high-pressure tube at a temperature of 50° C. The mixture of aqueous solution and excess hydrogen leaving the high-pressure tube was passed via a cooler into a separator from which the hydrogen, after using the consumed amount, was pumped back into the preheater together with still-unhydrogenated solution and from there into the high-pressure tube. The clear solution was let down, filtered via a fine filter, concentrated to a sugar alcohol content of approximately 80% in a falling-film evaporator and then completely crystallized in a vacuum crystallizer. The fine crystal powder obtained was composed of a mixture of α-D-glucopyranosido-1,6-mannitol and α-D-glucopyranosido-1,6-sorbitol in a ratio of 1:1. The water content was 5%. The mixture of the two stereoisomeric sugar alcohols was otherwise highly pure (degree of purity: 99.6%). The content of unhydrogenated α-D-glucopyranosido-1,6-fructose was ≦0.1%. The content of sorbitol was ≦0.1%. Mannitol could not be detected. The catalyst was as effective as ever even after a service life of 3822 hours.

Example 2

600 ml of a 40%-strength aqueous solution of α-D-glucopyranosido-1,6-fructose which had a pH of 8.5 were hydrogenated per hour by means of a high-pressure tube as in Example 1, but composed of N 9 high-pressure steel, at a temperature of 65° C. and a hydrogen pressure of 200 bar in reversed hydrogen flow, as described in Example 1. The catalyst had been produced by tabletting powder of an Ni/Zr alloy having a Zr content of 14.9% and an Al content of 10.5%. With a cylinder height of 5 mm and a diameter of 5 mm, the tablets had a compressive strength of 75 N and an internal surface area of 81 m²/g. After a service life of 1216 hours with unreduced effectiveness of the catalyst, the content of α-D-glucopyranosido-1,6-mannitol and α-D-glucopyranosido-1,6-sorbitol of the reaction mixture evaporated to dryness in a rotary evaporator was 99.6%. The content of unhydrogenated α-D-glucopyranosido-1,6-fructose was <0.1%. The content of sorbitol was 0.1%. The content of mannitol was 0.02%.

Example 3

An equally large amount of a 55%-strength aqueous solution of α-D-glucopyranosido-1,6-fructose which had a pH of 8.5 was hydrogenated per hour in a high-pressure tube as in Example 1 at a temperature of 45° C. and a hydrogen pressure of 300 bar in the same way as in Example 1. The catalyst had been produced by tabletting a powdered Ni/Fe/Zr alloy. The alloy contained an Fe proportion in Ni of 5% and a Zr proportion of 10.9%. With a cylinder height of 3 mm and a diameter of 3 mm, the tablets had a compressive strength of 103 N and a surface area of 95 m²/g. The 1:1 mixture obtained in a vacuum crystallizer of α-D-glucopyranosido-1,6-mannitol and α-D-glucopyranosido-1,6-sorbitol had a degree of purity of ≧99.5%. The content of unconverted α-D-glucopyranosido-1,6-fructose was <0.1%. The sorbitol content was 0.1%. The proportion of mannitol was 0.02%. The catalyst was as effective as ever after a service life of 1206 hours.

Example 4

An equally large amount of a 45%-strength aqueous solution of α-D-glucopyranosido-1,6-fructose which had a pH of 6.5 was hydrogenated in a high-pressure tube as in Example 1 at a temperature of 55° C. and a hydrogen pressure of 200 bar in the same way as in Example 1. The catalyst had been produced by tabletting a powdered Ni/Zr alloy and a powdered Ni/Ti alloy and had a Zr content of 12.1% and a Ti content of 5.8%. With a cylinder height of 5 mm and a diameter of 5 mm, the tablets had a compressive strength of 103 N and an internal surface area of 81 m²/g. The mixture obtained in a rotating vacuum tube of α-D-glucopyranosido-1,6-mannitol and α-D-glucopyranosido-1,6-sorbitol had a degree of purity of >99.5%. The content of unconverted α-D-glucopyranosido-1,6-fructose was <0.1%. The sorbitol content was 0.1%. Mannitol could not be detected. The catalyst was still as effective as ever after a service life of 4689 hours.

Example 5

An equally large amount of a 40%-strength aqueous solution of α-D-glucopyranosido-1,6-fructose which had a pH of 6.5 was hydrogenated in a high-pressure tube as in Example 1 at a temperature of 65° C. and a hydrogen pressure of 300 bar in the same way as in Example 2. The catalyst had been produced by tabletting a powdered Ni/Zr/V/Al alloy having a Zr content of 14.9%, a V content of 6.4% and an Al content of 10.4%. With a cylinder height of 5 mm and a diameter of 5 mm, the tablets had a compressive strength of 95 N and an internal surface area of 78 m²/g. The 1:1 mixture obtained in a vacuum crystallizer of α-D-glucopyranosido-1,6-mannitol and α-D-glucopyranosido-1,6-sorbitol had a degree of purity of >99.5%. The content of unconverted α-D-glucopyranosido-1,6-fructose was 0.1%. The sorbitol content was 0.1%. The proportion of mannitol was 0.02%. The catalyst was still as effective as ever after a service life of 1618 hours.

Example 6

An equally large amount of a 45%-strength aqueous solution of α-D-glucopyranosido-1,6-fructose which had a pH of 6.5 was hydrogenated in a high-pressure tube as in Example 1 at a temperature of 55° C. and a hydrogen pressure of 150 bar in the same way as in Example 1. The catalyst had been produced by tabletting a powdered Ni/V alloy which also contained Al. The alloy had a V content of 6.1% and an Al content of 9.4%. With a cylinder height of 5 mm and a diameter of 5 mm, the tablets had a compressive strength of 95 N and an internal surface area of 68 m²/g. The 1:1 mixture obtained in a rotary vacuum tube of α-D-glucopyranosido-1,6-mannitol and α-D-glucopyranosido-1,6-sorbitol had a degree of purity of >99.5%. The content of unreacted α-D-glucopyranosido-1,6-fructose was 0.1%. The sorbitol content was 0.05%. Mannitol could not be detected. The catalyst was still as effective as ever after a service life of 918 hours.

What is claimed is:

1. A process for preparing an equimolar mixture of α-D-glucopyranosido-1,6-mannitol and α-D-glucopyranosido-1,6-sorbitol from α-D-glucopyranosido-1,6fructose by catalytic hydrogenation in aqueous solution with hydrogen at elevated pressure and at elevated temperature, comprising carrying out the hydrogenation continuously at a hydrogen pressure of 100 to 400 bar and a temperature of 20 to 80° C. using the fixed-bed process over support-free molded bodies used as hydrogenation catalysts, having a compressive strength of 20 to 220 N and an internal surface area of 10 to 95 m²/g and composed of
   (i) one or more elements selected from the group consisting of iron, cobalt and nickel, which element or elements is/are alloyed with
   (ii) one or more elements selected from the group consisting of titanium, zirconium and hafnium, or one or more elements selected from the group consisting of vanadium, niobium and tantalium, or with one or more elements selected from the group consisting of titanium, zirconium and hafnium, and one or more elements selected from the group consisting of vanadium, niobium and tantalium, which have activating action.

2. The process of claim 1, wherein the molded bodies have a proportion by weight of said one or more elements selected from the group consisting of iron, cobalt and nickel of at least 50%.

3. The process of claim 2, wherein the proportion of said elements selected from the group consisting of iron, cobalt and nickel is at least 60% by weight.

4. The process of claim 3, wherein the proportion of said elements selected from the group consisting of iron, cobalt and nickel is at least 70% by weight.

5. The process of claim 1, wherein the molded bodies have a proportion by weight of said one or more elements selected from the group consisting of titanium, zirconium and hafnium of at least 1.5%.

6. The process of claim 5, wherein the proportion of said one or more elements selected from the group consisting of titanium, zirconium and hafnium is at least 3.0% by weight.

7. The process of claim 6, wherein the proportion of said one or more elements selected from the group consisting of titanium, zirconium and hafnium is at least 6.0% by weight.

8. The process of claim 1, wherein the molded bodies have dimensions of 3 to 7 mm.

9. The process of claim 1, wherein, the molded bodies further comprise one or more elements selected from the group consisting of aluminum, silicon and manganese with a proportion by weight of up to 20%.

10. The process of claim 9, wherein the proportion of said one or more elements selected from the group consisting of aluminum, silicon and manganese is up to 18% by weight.

11. The process of claim 10, wherein the proportion of said one or more elements selected from the group consisting of aluminum, silicon and manganese is up to 15% by weight.

12. The process of claim 9, wherein the molded bodies have a proportion by weight of not more than 12% aluminum and not more than 5% of one or more elements selected from the group consisting of silicon and manganese.

13. The process of claim 1, wherein the molded bodies have a compressive strength of 110–220 N.

14. The process of claim 1, wherein the hydrogenation of the α-D-glucopyranosido-1,6-fructose is carried out in a solution having a concentration of α-D-glucopyranosido-1,6-fructose of 15 to 60% by weight and at a pH of 4.5 to 11.5.

15. The process of claim 14, wherein said concentration is 40 to 55% by weight.

16. The process of claim 14, wherein the pH is 5 to 8.5.

17. The process of claim 1, wherein the hydrogenation is carried out at an $H_2$ pressure of 200 to 300 bar.

18. The process of claim 1, wherein the hydrogenation is carried out at 40 to 70° C.

* * * * *